United States Patent [19]

Barberet et al.

[11] Patent Number: Plant 5,789

[45] Date of Patent: Aug. 26, 1986

[54] CARNATION NAMED LONDAISON

[75] Inventors: Nicole Barberet; Yves Ducloux, both of Antibes, France

[73] Assignee: Laboratoire de Physiologie Vegetale de la Londe, La Londe, France

[21] Appl. No.: 613,715

[22] Filed: May 24, 1984

[51] Int. Cl.[4] ..... A01H 5/00

[52] U.S. Cl. ..... Plt./71

[58] Field of Search ..... Plt./71

*Primary Examiner*—James R. Feyrer

*Attorney, Agent, or Firm*—Charles W. Rummler; John B. Lungmus

[57] ABSTRACT

A new variety of spray carnation distinguished by its profuse production of small, medium pink flowers of a full, well shaped character having a rounded or dome-like form, and by its vigorous, upright and well branched growth habit reaching an average height of about 85 cm. with abundant foliage.

1 Drawing Figure

BACKGROUND OF THE INVENTION

Our new spray carnation plant originated as a seedling resulting from our crossing of two unnamed and unpatented varieties selected from our collection of spray carnations maintained at our laboratory at La Londe, Les Maures, Var., France. This crossing was done with the object of developing a new, medium pink colored carnation having good flower form and growth characteristics suitable for commercial greenhouse culture. This particular seeding was selected for propagation and test because of its apparently strong growth habit and flower production and propagation of this particular seedling, by means of cuttings from the parent plant, was done by us at La Londe and carried through several successive generations whereby it was shown that the novel characteristics of this new plant were fully retained from generation to generation and appeared to be firmly fixed. Commercial production of plants of this new variety, by in vitro propagation and cuttings, is carried on by us at La Londe.

DESCRIPTION OF THE DRAWINGS

Our new variety of spray carnation is illustrated by the accompanying full color photographic drawing, which shows the upper portions of a typical flowering stem of the new variety with buds in several stages of opening, as well as newly opened fully developed flowers, the color rendition being as nearly true as it is reasonably possible to obtain by conventional commercial photographic procedures.

DESCRIPTION OF THE NEW PLANT

The following is a detailed description of our new spray carnation variety as observed on greenhouse grown plants in the late Fall of 1983, the color designations being according to The R.H.S. Colour Chart published by The Royal Horticultural Society of London, England.

THE PLANT

Origin: Seedling.

Parentage:

*Seed parent.*—Unnamed and unpatented Variety No. 416 MP;

*Pollen parent.*—Unnamed and unpatented Variety No. 73 MV 2; these parent plants having been selected from our collection of carnation plants, duly recorded and maintained for breeding purposes, at our laboratory at La Londe, France.

Classification:

*Botanic.*—*Dianthus caryophyllus L.*

*Commercial.*—Spray carnation.

Form: Bush of tall, erect shape with at least four stems emitted near the ground.

Height: About 85 cm.

Growth: Vigorous and erect and very well branched.

Branching character: Each stem has 4 or 5 secondary branches (pedicels) which may bear one or more supplementary branches.

Foliage:

*Quantity.*—Abundant.

*Number of leaves.*—At least 120.

*Leaf size.*—About 11.5 cm. long and 0.7 cm. wide, taken at the seventh node.

Leaf shape: Amplexicaul with elongate body terminating with an acute apex and having straight margins slightly curved upwardly.

Texture: Leathery.

Ribs, veins and rachis: Hardly noticeable.

Color:

*Upper side.*—189A.

*Under side.*—189A.

THE BUD

Form: Generally cylindrical with ovate shaped and pointed top portion.

Size: Small.

*Diameter.*—1.2 cm. in average.

*Length.*—About 2.4 cm. in average.

Opening rate: Normal.

Color:

*When sepals first divide.*—Slightly deeper than in full bloom.

*When petals begin to unfurl.*—Slightly deeper than in full bloom.

Sepals:

*Number.*—5 to 6.

*Shape.*—Wide and joined at the lower part and having an apex of acute form.

*Character.*—The sepals stand up when the flowers open.

*Color.*—Inside — Greenish white. Outside — 144A and 145A.

*Striae.*—Sepals are longitudinally striated.

Calyx:

*Shape.*—Cylindrical and long.

*Aspect.*—Smooth.

*Splitting.*—The calyx rarely splits.

Flower stem:

*Length.*—In average, about 45 cm.

*Character.*—Erect and rigid.

*Color.*—191A.

THE FLOWER

Blooming habit: Recurrent the year around blooming profusely, but with a tendency to give fewer blooms in the Fall season.

Size of bloom: Small.

*Diameter.*—In average, about 6 cm. with a depth of about 4 cm.

Borne: In cluster, with 4 or 5 florets opening simultaneously.

Shape: High centered when bloom first opens becoming generally dome-shaped when bloom matures.

Petalage:

*Number of petals.*—In average, about 30.

*Arrangement.*—Imbricated.

*Form.*—Fan-shaped with wide and deeply serrated apex margin.

*Texture.*—Soft.

*Appearance.*—Satiny.

*Color.*—Outer and Inside Petals: Body —55D. Base — Greenish white. Reverse side — 56B.

Petaloids: Very rare.

*Size.*—Smaller than petals.

*Color.*—Same as petals.

Flower stem: In average, about 45 cm., cut at the tenth node.

*Character.*—Upright and of very good strength.

Discoloration after full bloom: Rather strong fading.

Fragrance: Perceptible.

Persistence: The flowers hang on and dry.

Lasting quality: At least ten days in vase keeping.

REPRODUCTIVE ORGANS

Stamens:

*Number.*—15 in average arranged around the ovary.

*Anthers.*—Size: Less than 4 mm. Color: Yellowish.

*Filaments.*—Color: Yellowish white.

Pistils:

*Number.*—3 to 4.

Styles:

*Color.*—Whitish.

Stigmas:

*Color.*—Whitish.

Character of ovaries: Smooth and greenish.

This new variety most nearly resembles the variety "Silvery Pink" (unpatented) and when compared to "Silvery Pink" and to "Lontrelos" (unpatented), the petals of our new variety are more serrated and the color is less uniform, being paler on the edge but with a more sustained base, and the foliage of our new variety is more abundant.

We claim:

1. The new and distinct spray carnation cultivar, substantially as herein shown and described, characterized in particular by its well formed but small blooms of a medium pink color which are produced profusely on intermittently blooming plants having a vigorous and tall growth habit.

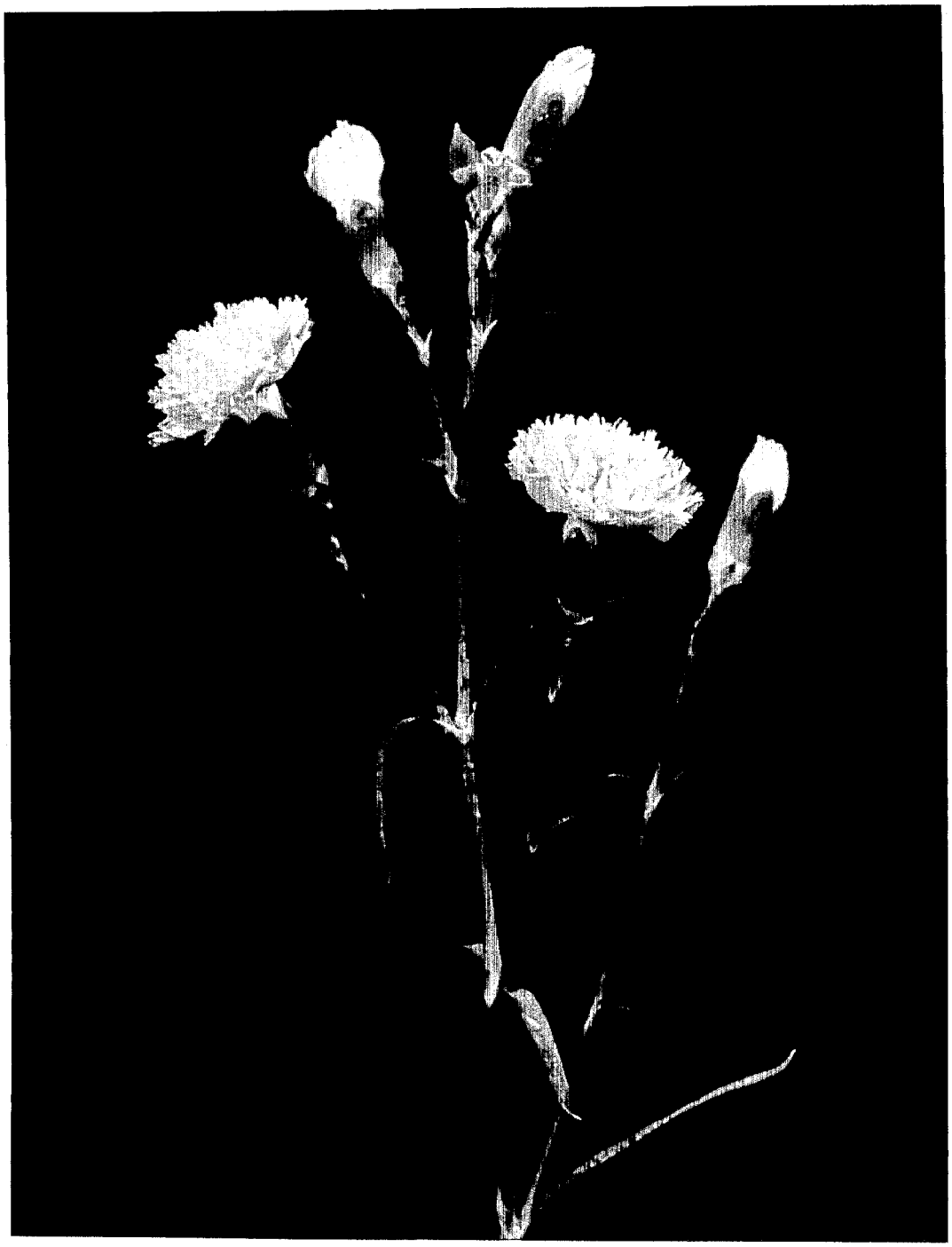

* * * * *